United States Patent [19]

Deutsch et al.

[11] Patent Number: 5,458,870
[45] Date of Patent: Oct. 17, 1995

[54] COMPOSITIONS FOR MAGNETIC RESONANCE IMAGING USING A MANGANESE OXALATE

[75] Inventors: Edward A. Deutsch, Maryland Heights; Dennis A. Moore, Ferguson, both of Mo.

[73] Assignee: Mallinckrodt Medical, Inc., St. Louis, Mo.

[21] Appl. No.: 233,494

[22] Filed: Apr. 26, 1994

Related U.S. Application Data

[60] Division of Ser. No. 862,865, Apr. 3, 1992, Pat. No. 5,330,742, which is a continuation-in-part of Ser. No. 699,848, Aug. 5, 1991.

[51] Int. Cl.[6] ........................................ A61B 5/055
[52] U.S. Cl. .................... 424/9.322; 436/173; 546/2; 556/49; 514/492; 514/836; 424/9.323
[58] Field of Search ........................... 424/9; 436/173, 436/806; 128/653.4, 654; 546/2; 556/49; 514/492, 836

[56] References Cited

U.S. PATENT DOCUMENTS

| | | | |
|---|---|---|---|
| 4,916,246 | 4/1990 | Felder et al. | 556/1 |
| 5,330,742 | 7/1994 | Deutsch et al. | 424/9 |

FOREIGN PATENT DOCUMENTS

90/03190  4/1990  WIPO.

OTHER PUBLICATIONS

Perlepes et al., Inorganic Chemistry 30:1665–1668 (1991).

Boyd et al., J. American Chemical Society 110:8537–8539 (1988).

Caneschi, A. et al., J. American Chemical Society 113:5873–5874 (1991).

de Vries, N. et al., American Chemical Society Meetings Abstract #795 (1992).

*Primary Examiner*—Gary E. Hollinden
*Attorney, Agent, or Firm*—Brian K. Stierwalt

[57] ABSTRACT

Methods and diagnostic compositions are disclosed for enhancing magnetic resonance imaging which utilize a paramagnetic metal cluster. Magnetic resonance contrast media containing $Z^+[Mn_{12}X_{12}(OYR)_{16}(L)_4]^-$, where OYR is an oxyacid such as benzoic acid, acetic acid, methyl sulphonic acid, methyl phosphonic acid; L is a neutral donor such as water, alcohol, pyridine, or other amines; X is a chalcogen, such as O or S; and Z is a pharmaceutically acceptable counterion are disclosed. Z may also be a paramagnetic counter ion, such as a high spin metal cluster. The paramagnetic cluster may optionally be complexed or conjugated to a carrier compound capable of altering the paramagnetic metal cluster's biodistribution, increasing its selectivity of tumor localization, and amplifying its proton relaxivity.

9 Claims, No Drawings

5,458,870

1

COMPOSITIONS FOR MAGNETIC RESONANCE IMAGING USING A MANGANESE OXALATE

CROSS REFERENCE TO RELATED APPLICATION

This is a divisional of U.S. application Ser. No. 07/862,865 filed Apr. 3, 1992, now U.S. Pat. No. 5,330,742 which is a CIP of U.S. application Ser. No. 07/699,848, filed Aug. 5, 1991.

BACKGROUND OF THE INVENTION

This invention relates to compositions for improving magnetic resonance imaging ("MRI"), magnetic resonance spectroscopy ("MRS"), and magnetic resonance spectroscopy imaging ("MRSI"). More particularly, the present invention relates to multinuclear cluster compositions as magnetic resonance contrast media ("MRCM").

The technique of MRI encompasses the detection of certain atomic nuclei (those possessing magnetic dipole moments) utilizing magnetic fields and radio-frequency radiation. It is similar in some respects to X-ray computed tomography ("CT") in providing a cross-sectional display of the body organ anatomy with excellent resolution of soft tissue detail. The technique of MRI is advantageously non-invasive as it avoids the use of ionizing radiation.

The hydrogen atom, having a nucleus consisting of a single unpaired proton, has the strongest magnetic dipole moment of any nucleus. Since hydrogen occurs in both water and lipids, it is abundant in the human body. Therefore, MRI is most commonly used to produce images based upon the distribution density of protons and/or the relaxation times of protons in organs and tissues. Other nuclei having a net magnetic dipole moment also exhibit a nuclear magnetic resonance phenomenon which may be used in MRI, MRS, and MRSI applications. Such nuclei include carbon-13 (six protons and seven neutrons), fluorine-19 (9 protons and 10 neutrons), sodium-23 (11 protons and 12 neutrons), and phosphorus-31 (15 protons and 16 neutrons).

While the phenomenon of MRI was discovered in 1945, it is only relatively recently that it has found application as a means of mapping the internal structure of the body as a result of the original suggestion of Lauterbur (*Nature*, 242, 190–191 (1973)). The fundamental lack of any known hazard associated with the level of the magnetic and radio-frequency fields that are employed renders it possible to make repeated scans on vulnerable individuals. Additionally, any scan plane can readily be selected, including transverse, coronal, and sagittal sections.

In an MRI experiment, the nuclei under study in a sample (e.g. protons, $^{19}F$, etc.) are irradiated with the appropriate radio-frequency (RF) energy in a controlled gradient magnetic field. These nuclei, as they relax, subsequently emit RF energy at a sharp resonance frequency. The resonance frequency of the nuclei depends on the applied magnetic field.

According to known principles, nuclei with appropriate spin when placed in an applied magnetic field (B, expressed generally in units of gauss or Tesla ($10^4$ gauss)) align in the direction of the field. In the case of protons, these nuclei precess at a frequency, F, of 42.6 MHz at a field strength of 1 Tesla. At this frequency, an RF pulse of radiation will excite the nuclei and can be considered to tip the net magnetization out of the field direction, the extent of this rotation being determined by the pulse, duration and energy. After the RF pulse, the nuclei "relax" or return to equilibrium with the magnetic field, emitting radiation at the resonant frequency. The decay of the emitted radiation is characterized by two relaxation times, $T_1$ and $T_2$. $T_1$ is the spin-lattice relaxation time or longitudinal relaxation time, that is, the time taken by the nuclei to return to equilibrium along the direction of the externally applied magnetic field. $T_2$ is the spin-spin relaxation time associated with the dephasing of the initially coherent precession of individual proton spins. These relaxation times have been established for various fluids, organs, and tissues in different species of mammals.

For protons and other suitable nuclei, the relaxation times $T_1$ and $T_2$ are influenced by the environment of the nuclei (e.g., viscosity, temperature, and the like). These two relaxation phenomena are essentially mechanisms whereby the initially imparted radio-frequency energy is dissipated to the surrounding environment. The rate of this energy loss or relaxation can be influenced by certain molecules or other nuclei which are paramagnetic. Chemical compounds incorporating these paramagnetic molecules or nuclei may substantially alter the $T_1$ and $T_2$ values for nearby nuclei having a magnetic dipole moment. The extent of the paramagnetic effect of the given chemical compound is a function of the environment within which it finds itself.

In MRI, scanning planes and sliced thicknesses can be selected. This selection permits high quality transverse, coronal and sagittal images to be obtained directly. The absence of any moving parts in MRI equipment promotes a high reliability. It is believed that MRI has a greater potential than CT for the selective examination of tissue characteristics. The reason for this being that in CT, X-ray attenuation and coefficients alone determine image contrast, whereas at least four separate variables ($T_1$, $T_2$, proton density, and flow) may contribute to the MRI signal. For example, it has been shown (Damadian, *Science*, 171, 1151 (1971)) that the values of the $T_1$ and $T_2$ relaxation in tissues are generally longer by about a factor of two (2) in excised specimens of neoplastic tissue compared with the host tissue.

By reason of its sensitivity to subtle physiochemical differences between organs and/or tissues, it is believed that MRI may be capable of differentiating different tissue types and in detecting diseases which induce physicochemical changes that may not be detected by X-ray or CT which are only sensitive to differences in the electron density of tissue.

From the foregoing, it would be a significant advancement in the art to provide physiologically compatible MRCM for enhancing images of body organs and tissues.

Such MRCM are disclosed and claimed herein.

SUMMARY OF THE INVENTION

The present invention provides methods and diagnostic compositions for improved magnetic resonance imaging utilizing high spin paramagnetic multinuclear clusters. As used herein, the term multinuclear clusters include metal clusters having two or more paramagnetic metal atoms. The high spin multinuclear clusters preferably have a spin value significantly greater than that of a single metal atom. Typical paramagnetic metal atoms which can be included in the clusters are Ta, Cr, W, Mn, Fe, Co, Ni, Cu, Pr, Nd, Sm, Y, Gd, Tb, Dy, Ho, and Er.

The metal clusters included in the diagnostic compositions may be ionic (anionic, cationic, or zwitterionic) or non-ionic. One currently preferred diagnostic composition within the scope of the present invention includes derivatives of the neutral metal cluster $Mn_{12}X_{12}(OYR)_{16}(L)_4$, where OYR is an oxyacid such as benzoic acid, acetic acid, methyl sulphonic acid, methyl phosphonic acid; L=a neutral donor such as water, alcohol, pyridine, or other amines; and X is a chalcogen, such as O or S. A specific example of the forgoing neutral metal cluster is $Mn_{12}O_{12}(O_2CPh)_{16}(H_2O)_4$. Such metal clusters are formulated into physiologically tolerable diagnostic compositions.

Also disclosed are methods of performing MR diagnostic procedures which involve administering to a warm-blooded animal a diagnostically effective amount of the above-described MRCM diagnostic compositions containing a suitable metal cluster and then exposing the warm-blooded animal to a MR procedure.

DETAILED DESCRIPTION OF THE INVENTION

The present invention provides methods and diagnostic compositions for improved magnetic resonance imaging utilizing paramagnetic multinuclear clusters. Possible multinuclear clusters for use in the diagnostic compositions of the present invention and methods of preparing the clusters are described in copending patent application Ser. No. 07/699,848, titled "Heavy Metal Clusters For Use As Imaging Agents," which is incorporated herein by reference. Such paramagnetic clusters represent the active ingredient of the disclosed diagnostic compositions.

Metal clusters are known in the art (F. A. Cotton, G. Wilkinson, *Advanced Inorganic Chemistry*, 4th Edition, Wiley & Sons, 1980, 1080–1112). Cotton and Wilkinson state that "A metal atom cluster may be defined as a group of two or more metal atoms in which there is substantial and direct bonding between the metal atoms." These clusters have found the greatest application either as catalysts or as models for metal surface-catalyzed reactions. Metal clusters of many paramagnetic elements are known and, in many instances, cluster-like compounds in which metal-metal bonding is weak or non-existent (ordinary polynuclear complexes) are also known. See, for example, U.S. Pat. No. 4,832,877 to Bino et al., WO 90/03190 to Ranney, and WO 91/14460 to Nycomed AS, which are incorporated herein by reference.

One currently preferred diagnostic composition within the scope of the present invention includes derivatives of the neutral metal cluster $Mn_{12}X_{12}(OYR)_{16}(L)_4$, where OYR is an oxyacid such as benzoic acid, acetic acid, methyl sulphonic acid, methyl phosphonic acid; L is a neutral donor such as water, alcohol, pyridine, or other amines; and X is a chalcogen, such as O or S. A specific example of the forgoing neutral metal cluster is $Mn_{12}O_{12}(O_2CPh)_{16}(H_2O)_4$, (X). This cluster may be prepared according to the procedure reported by Peter D. W. Boyd, et al., "Potential Building Blocks for Molecular Ferromagnets: $[Mn_{12}O_{12}(O_2CPh)_{16}(H_2O)_4]$ with a S=14 Ground State," *Journal of the American Chemical Society*, Vol. 110, pp. 8537–8539 (1988). Reduction of $Mn_{12}O_{12}(O_2CPh)_{16}(H_2O)_4$ with iodide yields a high spin anion. See Abstracts of 203rd Meeting of the *American Chemical Society*, San Francisco, Calif., Apr. 5–10, 1992. The anion is an example of a high spin metal cluster having a spin value of 19/2. By comparison, $Gd^{3+}$ has a spin value of 7/2.

$[Mn_{12}O_{12}(O_2CPh)_{16}(H_2O)_4]$ may be prepared with several different counter ions. For example, reduction with tetrapropyl ammonium and tetra phenyl phosphonium iodide salts yields $(n-Pr_4N)[Mn_{12}O_{12}(O_2CPh)_{16}(H_2O)_4]$ and $(Ph_4P)[Mn_{12}O_{12}(O_2CPh)_{16}(H_2O)_4]$, respectively. Reaction with KI in the presence of a paramagnetic cationic metal cluster, such as $[Mn_3O(O_2CR)_6L_3]$, where R is Me or Ph and L is a neutral ligand such as water or pyridine may yield a composition with two high-spin metal clusters, one cationic and one anionic.

For example, reaction of (I) with KI in the presence of $(ClO_4)$ $[Mn_3O(O_2CMe)_6(H_2O)_3]$ gives $[Mn_3O(O_2CMe)_6(H_2O)_3]^+[Mn_{12}O_{12}(O_2CPh)_{16}(H_2O)_4]^-$ plus potassium perchlorate and iodine.

The diagnostic compositions within the scope of the present invention may include a paramagnetic metal cluster that has been complexed with solubilizing ligands or functional groups. For ionic clusters in an aqueous formulation, pharmaceutically acceptable counter ions are required and these counter ions may be paramagnetic. In addition, the paramagnetic metal cluster may optionally be complexed or conjugated to carrier compounds which may increase the cluster's stability, alter its biodistribution, increase its selectivity of tumor localization, and amplify its proton relaxivity by slowing its rotational correlation time. Typical carrier compounds which may be used in the present invention include polymeric or microspheric carriers, liposome carriers, and hydroxyapatite carriers.

Possible polymeric or microspheric carriers are described in WO 90/03190 (incorporated by reference). Such carriers may be negatively charged, such as heparin, DTPA-dextrans, DTPA-hydroxyethyl starch, mono- or polyphosphonates and succinylated-dextrans; neutral, such as dextran and hydroxyethyl starch; or positively charged, e.g., polyhydroxylated quaternary amines. Where liposome carriers are utilized, the paramagnetic metal cluster may be internally entrapped by the liposome or externally bound to the liposome. For hydroxyapatite carriers, the paramagnetic cluster may be internally entrapped by the hydroxyapatite or externally bound to the hydroxyapatite particles.

The diagnostic compositions of this invention are preferably formulated in biocompatible solubilizing media for enteral or parenteral administration. The MRCM formulations may contain conventional pharmaceutical carriers and excipients appropriate for the type of administration contemplated.

For example, parenteral formulations imaging advantageously contain a sterile aqueous solution or suspension of a paramagnetic metal cluster MRCM according to this invention. Various techniques for preparing suitable pharmaceutical solutions and suspensions are known in the art. Such solutions also may contain pharmaceutically acceptable buffers, stabilizers, antioxidants, and electrolytes, such as sodium chloride. Parenteral compositions may be injected directly or mixed with a large volume parenteral composition for systemic administration.

Formulations for enteral administration may vary widely, as is well-known in the art. In general, such formulations include a diagnostically effective amount of a paramagnetic metal cluster MRCM in an aqueous solution or suspension. Such enteral compositions may optionally include buffers, surfactants, adjuvants, thixotropic agents, and the like. Compositions for oral administration may also contain flavoring agents and other ingredients for enhancing their organoleptic qualities.

The diagnostic compositions within the scope of the present invention are administered in doses effective to achieve the desired enhancement of the magnetic resonance image. Such doses may vary widely, depending upon the degree of fluorination, the organs or tissues which are the subject of the imaging procedure, the magnetic resonance imaging equipment being used, etc. Typical doses of the diagnostic compositions are in the range from about 0.005 to about 20 mmol/kg body weight, and preferably in the range from about 0.05 to about 5 mmol/kg body weight.

The diagnostic compositions of this invention are used in a conventional manner in magnetic resonance procedures. Compositions may be administered in a sufficient amount to provide adequate visualization, to a warm-blooded animal either systemically or locally to an organ or tissues to be imaged, and the animal then subjected to the MRI procedure. The compositions enhance the magnetic resonance images obtained by these procedures.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A sterile diagnostic composition suitable for enteral or parenteral administration to a warm-blooded animal comprising:

a diagnostically effective amount of a paramagnetic metal cluster having a formula: $Z^+[Mn_{12}X_{12}(OYR)_{16}(L)_4]^-$, where OYR is an oxyacid such as benzoic acid, acetic acid, methyl sulphonic acid, methyl phosphonic acid; L is a neutral donor such as water, alcohol, pyridine, or other amines; X is a chalcogen, such as O or S; and Z is a pharmaceutically acceptable counterion; and a pharmaceutically acceptable carrier.

2. A diagnostic composition as defined in claim 1, wherein Z is a paramagnetic counterion.

3. A diagnostic composition as defined in claim 2, wherein Z is $[Mn_3O(O_2CR)_6L_3]^+$, where R is Me or Ph and L is a neutral ligand.

4. A diagnostic composition as defined in claim 3, wherein Z is $[Mn_3O(O_2CMe)_6(H_2O)_3]^+$.

5. A diagnostic composition as defined in claim 1, wherein the paramagnetic metal cluster is complexed or conjugated to a carrier compound capable of altering the paramagnetic metal cluster's biodistribution, increasing its selectivity of tumor localization, and amplifying its proton relaxivity.

6. A diagnostic composition as defined in claim 5, wherein the carrier compound comprises a polymeric carrier.

7. A diagnostic composition as defined in claim 5, wherein the carrier compound comprises a microspheric carrier.

8. A diagnostic composition as defined in claim 5, wherein the carrier compound comprises a liposome carrier.

9. A diagnostic composition as defined in claim 5, wherein the carrier compound comprises a hydroxyapatite carrier.

* * * * *